(12) United States Patent
Bernhard et al.

(10) Patent No.: US 10,620,178 B2
(45) Date of Patent: Apr. 14, 2020

(54) OPTICAL SENSOR

(71) Applicant: Endress+Hauser Conducta GmbH+Co. KG, Gerlingen (DE)

(72) Inventors: Ralf Bernhard, Stuttgart (DE); Detlev Wittmer, Maulburg (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 16/215,773

(22) Filed: Dec. 11, 2018

(65) Prior Publication Data

US 2019/0187118 A1 Jun. 20, 2019

(30) Foreign Application Priority Data

Dec. 15, 2017 (DE) .................. 10 2017 130 141

(51) Int. Cl.
*G01N 21/64* (2006.01)
*G01N 21/51* (2006.01)
*G01N 33/18* (2006.01)

(52) U.S. Cl.
CPC ......... *G01N 33/1833* (2013.01); *G01N 21/51* (2013.01); *G01N 21/64* (2013.01)

(58) Field of Classification Search
CPC ..... G01N 21/51; G01N 21/64; G01N 33/1833
See application file for complete search history.

(56) References Cited

U.S. PATENT DOCUMENTS

| | | | |
|---|---|---|---|
| 2005/0135546 A1* | 6/2005 | Ponstingl ............... | G01N 21/55 376/305 |
| 2006/0227319 A1* | 10/2006 | Imura .................... | G01N 21/64 356/256 |
| 2015/0090900 A1* | 4/2015 | Banks ................. | G01N 21/645 250/432 R |

* cited by examiner

*Primary Examiner* — Mark R Gaworecki
(74) *Attorney, Agent, or Firm* — Christopher R. Powers; PatServe

(57) ABSTRACT

The present disclosure relates to an optical sensor comprising at least one light source for emitting transmission light into a medium, at least one detector, wherein the transmission light is at least partially converted in the medium by fluorescence into fluorescent light and the detector receives the fluorescent light, wherein a first receiver signal can be generated from the fluorescent light, and wherein a first measured value can be determined from the first receiver signal, wherein the transmission light is at least partially scattered by means of the medium to form scattered light, and the detector receives the scattered light, wherein a second receiver signal can be generated from the scattered light, and wherein a second measured value can be determined from the second receiver signal. The present disclosure further relates to a method for determining a first and second measured value of a medium.

12 Claims, 2 Drawing Sheets

OPTICAL SENSOR

CROSS-REFERENCE TO RELATED APPLICATION

The present application is related to and claims the priority benefit of German Patent Application No. 10 2017 130 141.0, filed on Dec. 15, 2017, the entire contents of which are incorporated herein by reference.

TECHNICAL FIELD

The present disclosure relates to an optical sensor designed to determine a measured value of a measurand of process automation technology in a medium.

BACKGROUND

The sensor is a fluorescence sensor, for example. In order to measure fluorescence, one generally irradiates the medium with a short-wavelength excitation light and detects the longer-wavelength fluorescent light produced by the medium. A fluorescence measurement is typically arranged as depicted in FIG. 1.

The fluorescence sensor 3 comprises a light source 1 and a receiver 2. The light source 1 transmits transmission light; the receiver 2 receives reception light. Since the fluorescent light is radiated in all spatial directions, the light paths of the transmission and reception light can in principle be at any angle α to each other.

Fluorescent and non-fluorescent particles scatter the transmission light. This scattered transmission light can also enter the receiver 2 and disturb the measurement of the fluorescence and lead to erroneous measurements.

SUMMARY

The aim of the present disclosure is to minimize errors in the measurement of fluorescence.

This aim is achieved by an optical sensor comprising: at least one light source for emitting transmission light into a medium; at least one detector, wherein the transmission light is at least partially converted in the medium by fluorescence into fluorescent light and the detector receives the fluorescent light, wherein a first receiver signal can be generated from the fluorescent light and wherein a first measured value can be determined from the first receiver signal, wherein the transmission light is at least partially scattered by means of the medium to form scattered light, and the detector receives the scattered light, wherein a second receiver signal can be generated from the scattered light, and wherein a second measured value can be determined from the second receiver signal.

As mentioned, scattered particles can interfere with the measurement of fluorescence. However if the turbidity is known, which is measured by scattered particles, this effect can be compensated. Frequent scattering moreover reduces the penetration depth of the transmission light into the medium and also impedes the return path of the fluorescent light to the receiver. This effect can also be compensated with knowledge of the turbidity.

An advantage results from the fact that a single sensor measures two different parameters: fluorescence and turbidity. Both are measurands which are important at the same time, for example, in sewage treatment plants. In one embodiment, the entire optical sensor is accommodated in a single housing.

An advantage is that by knowing the turbidity and the fluorescence, fluorescent and non-fluorescent particles can now be distinguished.

In one embodiment, the light source emits at least UV radiation and infrared radiation.

In one embodiment, the light source is a UV flash lamp with emission in the infrared range.

In one embodiment, the light source is designed as an LED.

In one embodiment, the light source comprises a visible light filter. As a result, only UV light and IR light enter the medium to be measured. The IR light does not cause fluorescence and thus serves to measure turbidity. In one embodiment, the filter for the fluorescence measurement is a bandpass that lets only visible light pass. Otherwise, the receiver receives both visible fluorescent light as well as visible scattered light.

In one embodiment, the sensor comprises a first light source for emitting the first transmission light, which is converted in the medium by fluorescence into fluorescent light, and a second light source for emitting the second transmission light, which is converted by means of the medium into scattered light.

In one embodiment, the first and second light sources are arranged on different optical axes with respect to the medium.

In one embodiment, the light source emits UV light having a wavelength of 200-400 nm.

In one embodiment, the at least one detector is configured as precisely one detector. The scattered light is scattered back from the sample virtually without delay, in contrast to the time-delayed fluorescent light. It is thus possible with only one detector to detect first the scattered light and then the fluorescent light.

In one embodiment, the detector is a spectrometer, wherein the spectrometer is configured to spectrally separate the fluorescent light and the scattered light and to determine the first and second measured values therefrom.

In one embodiment, the detector is a photodiode. In one embodiment, the detector comprises a photodiode with a filter for attenuating the transmission light.

In one embodiment, the sensor comprises a first detector for fluorescent light and a second detector for scattered light.

In one embodiment, the first and/or second light source and the first and/or second detector are arranged in such a way that at least the transmission light that is converted into scattered light and the scattered light form an angle of 90°.

In one embodiment, the sensor is designed to determine the oil-in-water content.

The aim is achieved by a method for determining a first and second measured value of a medium by means of an optical method, comprising the steps of: emitting transmission light into a medium; detecting fluorescent light converted in the medium by fluorescence from the transmission light; determining the first measured value from the fluorescent light; detecting scattered light scattered from the transmission light by means of the medium; and determining the second measured value from the scattered light.

BRIEF DESCRIPTION OF THE DRAWINGS

This is explained in more detail with reference to the following figures.

In the figures, the same features are identified with the same reference symbols.

DETAILED DESCRIPTION

Figure 1:
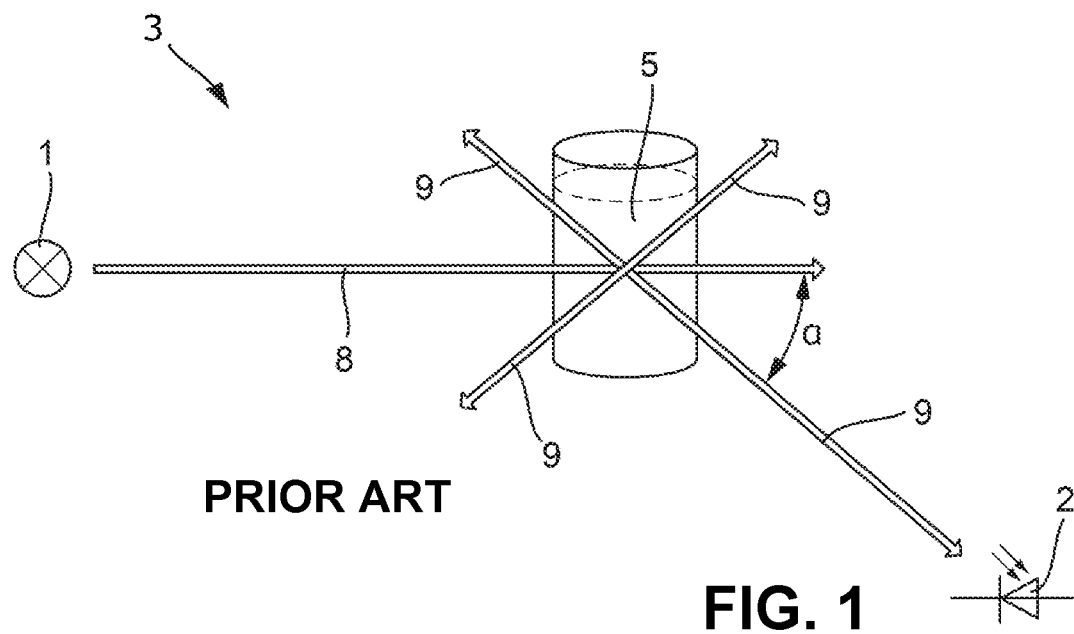
FIG. 1 shows a schematic diagram of a fluorescence measurement arrangement according to the prior art.
Figure 2:
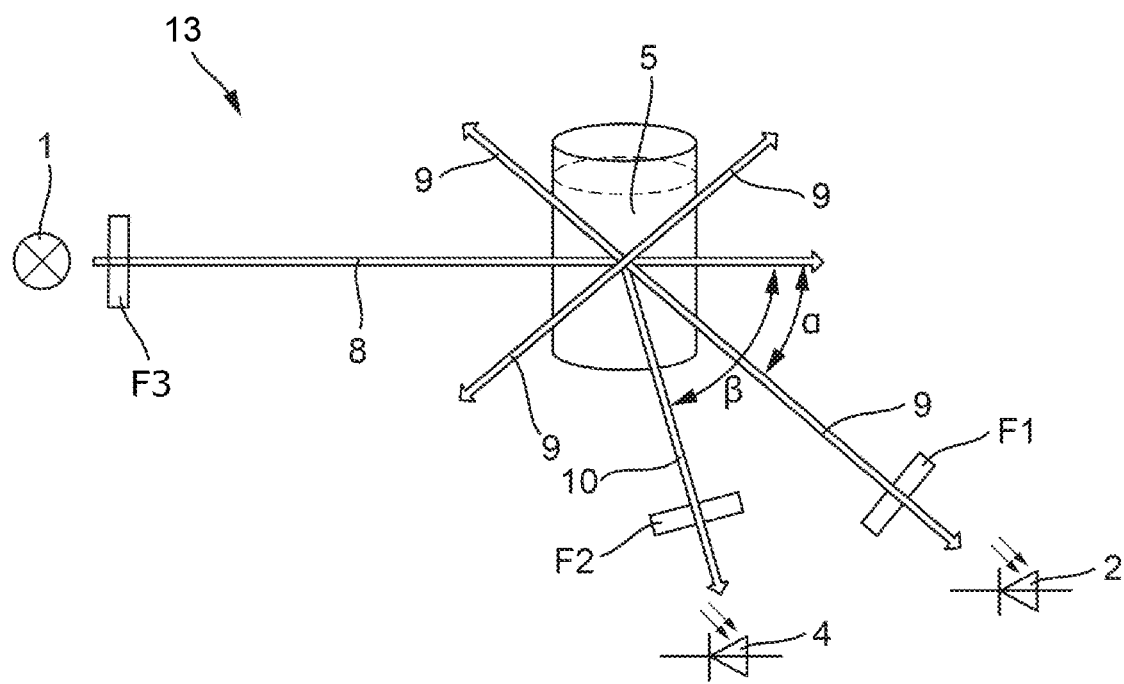
FIG. 2 shows a schematic diagram of a sensor according to the present disclosure.

In the following, only the differences from the above-described prior art are discussed. The claimed sensor in its entirety bears the reference symbol 3 and is shown in a schematic diagram in FIG. 2. The sensor 13 is basically suitable for determining the oil-in-water content of a medium 5.

A light source 1 transmits transmission light 8 towards the medium 5. The light source may be a UV light source which transmits light having a wavelength of 200-400 nm. Such a light source 1 is designed as a UV flash lamp, for example. The light source 1 can also be designed as an LED. The UV flash lamp emits in the spectral range from UV to IR.

In the beam path after the light source 1, the arrangement comprises a filter F3 which suppresses the visible portion of the light. Together with the filter F3, the light source 1 then emits only UV and IR, not VIS light.

The transmission light 8 is partially converted in the medium 5 by fluorescence into fluorescent light 9. The fluorescent light 9 takes the path towards the receiver 2 which is arranged at an arbitrary angle α. The angle α is the angle between the transmission light 8 and the fluorescent light 9. The receiver 2 may be a photodiode. The optical path may also contain one or more lenses or filters F1. The receiver 2 can likewise be designed as a spectrometer.

In one embodiment, the sensor 13 comprises a second receiver 4. The transmission light 8 is scattered in the medium 5 and measured at an angle β as scattered light 10. The angle β may, for example, be 90°. The receiver 4 may also be a photodiode. This optical path may also comprise a filter F2. The receiver 4 can likewise be designed as a spectrometer.

Since the scattered light 10 is scattered back from the sample virtually without delay in contrast to the time-delayed fluorescent light 9, it is possible with only a single receiver 2 to first detect the scattered light 10 as a measure of the turbidity and then the fluorescent light 9. In this embodiment in particular, excitation takes place with a flash, for example by means of a flash lamp or LED.

The receivers 2 and/or 4 convert the received fluorescent light 9 and scattered light 10 into corresponding receiver signals, wherein a first and a second measured value respectively, i.e., for example, the oil-in-water content and the turbidity of the medium 5, can then be determined therefrom.

The light source(s) and receiver(s) are controlled via a data processing device, such as a microcontroller (not shown).

This first example thus comprises a light source 1 and two receivers 2, 4.

The light source 1, prism 6, and receiver 2 are arranged in a single housing. The housing may be tube-shaped, having a diameter of 35-75 mm. The housing comprises an optical window which is permeable at least to transmission light 8 and fluorescent light 9. The distance from the light source 1 or the receiver 2 to the window is about 2-6 cm.

The filter or filters F1, F2 are configured as wavelength filters, more precisely as interference filters. The filter F1 filters out the visible fluorescent light and suppresses the UV excitation light. The filter F2 filters out IR light and suppresses visible light and UV light.

Figure 3:
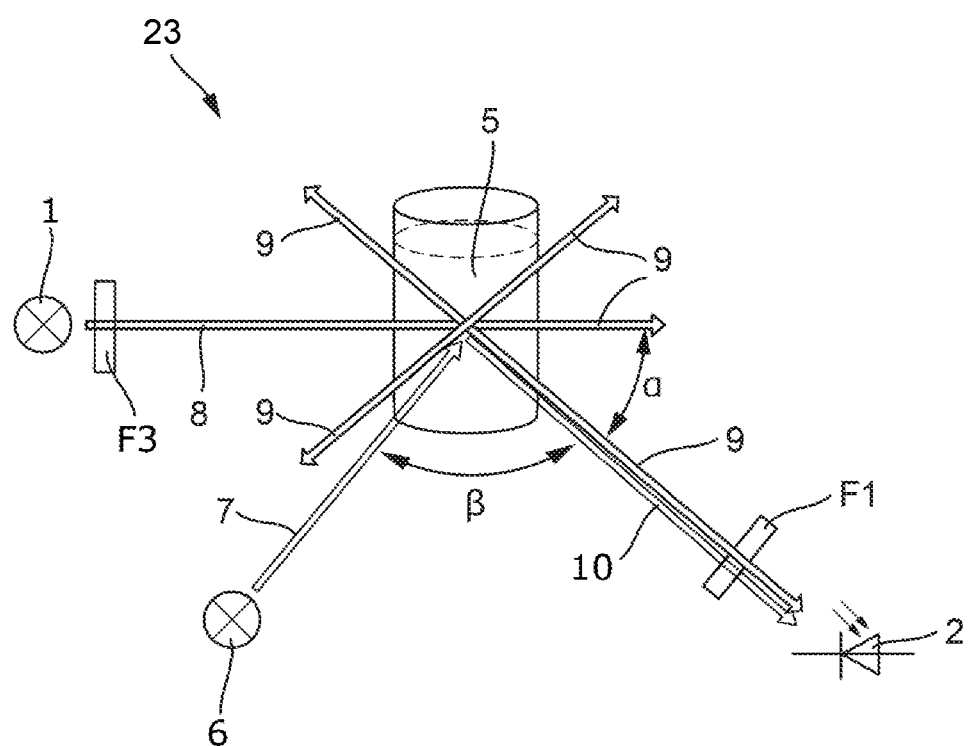
FIG. 3 shows a schematic diagram of another embodiment of a sensor according to the present disclosure.

The second embodiment, a sensor 23 in FIG. 3, comprises two light sources 1, 6 and a receiver 2. Light source 1 transmits transmission light 8 in the UV range, and light source 6 transmits transmission light 7 in the infrared range. The transmission light 8 is partially converted in the medium 5 by fluorescence into fluorescent light 9. The fluorescent light 9 takes the path towards the receiver 2, which is arranged at any angle α. The transmission light 7 is scattered in the medium 5 and measured at an angle β as scattered light 10. The optical path also comprises at least one filter F1. The light source 1 and the light source 6 are not arranged on the same optical axis with respect to the medium 5.

In this example, the receiver 2 is designed as a spectrometer. The spectrally unshifted scattered light 10 and the spectrally shifted fluorescent light 9 can be separated using the spectrometer. The first and second measured values can then be determined from the scattered light 10 and the fluorescent light 9, wherein the turbidity and fluorescence can then be determined therefrom.

The spectrometer is designed to receive the spectral range of at least the transmission light 7, 8, that is to say also the scattered light 10, and the fluorescent light 9.

In one embodiment, the receiver 2 in FIG. 3 is also configured as a photodiode with a filter, wherein the filter suppresses the UV excitation light. The UV light source 1 and IR light source 6 are not operated simultaneously, so that UV and IR in this case must not be separated optically. In the embodiment as a spectrometer, the fluorescent light is not only measured integrally but is spectrally decomposed.

The invention claimed is:

1. An optical sensor comprising:
a first light source adapted to emit a first transmission light into a medium; and
at least one detector adapted to receive light and generate receiver signals corresponding to the received light,
wherein the first transmission light is at least partially converted in the medium due to fluorescence into fluorescent light and the at least one detector is arranged to receive the fluorescent light, wherein a first receiver signal is generated by the at least one detector based on the fluorescent light, and wherein a first measured value is determined from the first receiver signal,
wherein the first transmission light is at least partially scattered by the medium as scattered light and the at least one detector is arranged to receive the scattered light, wherein a second receiver signal is generated by the at least one detector based on the scattered light, and wherein a second measured value is determined from the second receiver signal; and
wherein the at least one detector is a spectrometer configured to spectrally separate the fluorescent light and the scattered light and to determine the first and second measured values therefrom.

2. The optical sensor of claim 1, wherein the first light source emits at least UV radiation and infrared radiation.

3. The optical sensor of claim 2, wherein the first light source is a UV flash lamp with at least partial emission in the infrared range.

4. The optical sensor of claim 1, wherein the first light source includes a filter configured to filter visible light from the first transmission light.

5. The optical sensor of claim 1, further comprising a second light source adapted to emit a second transmission light that is converted by the medium into scattered light.

6. The optical sensor of claim 5, wherein the first light source and the second light source are arranged on different optical axes with respect to the medium.

7. The optical sensor of claim 1, wherein the at least one detector includes only one detector.

8. The optical sensor of claim 1, wherein the at least one detector includes a first detector adapted to receive fluorescent light and a second detector adapted to receive scattered light.

9. The optical sensor of claim 8, wherein the first light source and/or the second light source and the first detector and/or the second detector are arranged such that at least the transmission light converted into scattered light and the scattered light form an angle of 90°.

10. A method for determining first and second measured values of a medium, the method comprising:
emitting transmission light into a medium;
detecting fluorescent light converted in the medium due to fluorescence from the transmission light;
determining a first measured value from the fluorescent light;
detecting scattered light scattered by the medium from the transmission light; and
determining the second measured value from the scattered light,
wherein the detecting of the fluorescent light and the detecting of the scattered light is performed using a spectrometer configured to spectrally separate the fluorescent light and the scattered light.

11. The method of claim 10, wherein the first measured value is an oil-in-water content of the medium.

12. The method of claim 10, wherein the second measured value is a turbidity of the medium.

\* \* \* \* \*